(12) United States Patent
Yamada et al.

(10) Patent No.: US 9,038,626 B2
(45) Date of Patent: May 26, 2015

(54) LIQUID TANK FOR AEROSOL INHALATOR

(75) Inventors: Manabu Yamada, Tokyo (JP); Hiroshi Sasaki, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 403 days.

(21) Appl. No.: 13/618,324

(22) Filed: Sep. 14, 2012

(65) Prior Publication Data

US 2013/0019862 A1 Jan. 24, 2013

Related U.S. Application Data

(63) Continuation of application No. PCT/JP2011/057351, filed on Mar. 25, 2011.

(30) Foreign Application Priority Data

Mar. 29, 2010 (WO) .................. PCT/JP2010/055553

(51) Int. Cl.
| | |
|---|---|
| A61M 11/02 | (2006.01) |
| A61M 15/00 | (2006.01) |
| A61M 11/04 | (2006.01) |
| A24F 47/00 | (2006.01) |
| B05B 7/16 | (2006.01) |
| B05B 7/24 | (2006.01) |
| A61M 11/06 | (2006.01) |
| B05B 7/00 | (2006.01) |

(52) U.S. Cl.
CPC ............. *A61M 11/041* (2013.01); *A61M 11/06* (2013.01); *A24F 47/004* (2013.01); *B05B 7/0075* (2013.01); *B05B 7/1686* (2013.01); *B05B 7/2424* (2013.01); *B05B 7/2483* (2013.01); *A61M 11/042* (2014.02); *A61M 15/0093* (2014.02)

(58) Field of Classification Search
CPC ..... A61M 11/02; A61M 11/06; A61M 11/08; A61M 11/041; A61M 15/00; A61M 15/0001; A61M 15/009; A61M 15/0093
USPC ............................ 128/200.14–200.23, 203.12
See application file for complete search history.

(56) References Cited

U.S. PATENT DOCUMENTS

| | | | |
|---|---|---|---|
| 4,288,396 A | 9/1981 | Ottestad | |
| 5,388,574 A * | 2/1995 | Ingebrethsen | 128/203.17 |
| 2003/0015191 A1 * | 1/2003 | Armstrong et al. | 128/200.21 |
| 2003/0209238 A1 * | 11/2003 | Peters et al. | 128/200.14 |
| 2005/0023368 A1 * | 2/2005 | Valpey et al. | 239/1 |
| 2005/0115992 A1 | 6/2005 | Cohen et al. | |
| 2006/0118107 A1 * | 6/2006 | King | 128/200.23 |
| 2008/0156326 A1 * | 7/2008 | Belcastro et al. | 128/203.27 |
| 2009/0217924 A1 * | 9/2009 | Pearson | 128/200.14 |

FOREIGN PATENT DOCUMENTS

| | | |
|---|---|---|
| CN | 1205849 A | 1/1999 |
| CN | 1293580 A | 5/2001 |

(Continued)

*Primary Examiner* — Valerie L Skorupa
(74) *Attorney, Agent, or Firm* — Birch, Stewart, Kolasch & Birch, LLP (57) ABSTRACT

A liquid tank for an aerosol inhalator has a reservoir channel opening into air at one end thereof and containing flavor solution inside; a supply pipe connecting the other end of the reservoir channel to an inhalation passage of the aerosol inhalator and guiding the flavor solution to the inhalation passage through either one of inhalation pressure in the inhalation passage and capillary action; and an outflow valve located between the other end of the reservoir channel and the supply pipe, for allowing only the flow of the flavor solution running from the reservoir channel towards the supply pipe.

9 Claims, 7 Drawing Sheets

(56) References Cited

FOREIGN PATENT DOCUMENTS

| | | |
|---|---|---|
| CN | 101155604 A | 4/2008 |
| CN | 101522244 A | 9/2009 |
| JP | 11-89551 A | 4/1999 |
| JP | 2009-131367 A | 6/2009 |
| TW | 386021 B | 4/2000 |
| WO | WO 2009/069518 A1 | 6/2009 |
| WO | WO 2009/103510 A1 | 8/2009 |
| WO | WO 2009/103510 A8 | 8/2009 |

* cited by examiner

LIQUID TANK FOR AEROSOL INHALATOR

CROSS REFERENCE TO RELATED APPLICATIONS

This application is a Continuation of PCT International Application No. PCT/JP2011/057351 filed on Mar. 25, 2011, which claims priority under 35 U.S.C. §119(a) to International Application No. PCT/JP2010/055553 filed in Japan on Mar. 29, 2010, all of which are hereby expressly incorporated by reference into the present application.

TECHNICAL FIELD

The present invention relates to a liquid tank for supplying a flavor solution, and more specifically, to a liquid tank suitable for an aerosol inhalator which transforms the flavor solution into flavored aerosol and allows the user to inhale the flavored aerosol along with air.

BACKGROUND ART

An aerosol inhalator of this type is disclosed in Patent Documents 1 and 2 below. Both aerosol inhalators disclosed in Patent Documents 1 and 2 include an inhalation passage and a liquid tank storing a flavor solution. The liquid tank supplies the flavor solution to a predetermined position of the inhalation passage through inhalation pressure or capillary action in the inhalation passage. Such an aerosol inhalator eliminates the need for a drive source, namely, a supply pump, for supplying the flavor solution to the supply position, which makes it possible to downsize the aerosol inhalator.

PRIOR ART DOCUMENT

Patent Document

Patent Document 1: Unexamined Japanese Patent Publication No. 11-89551 (JP 11-89551 A)
Patent Document 2: International Publication No. 2009/069518 (WO 2009/069518 A1)

SUMMARY OF THE INVENTION

Problems to be Solved by the Invention

The liquid tank of Patent Document 1 has a tank body, a supply pipe extending upward from the liquid in the tank body to the inhalation passage, and a heater fixed to an outlet of the supply pipe. The position of the outlet of the supply pipe has to be at such height that enables the flavor solution to move upward in the supply pipe through capillary action. This considerably regulates the design and layout of the liquid tank.

When the liquid tank has a small remaining amount of the flavor solution or when the liquid tank is inclined, the velocity at which the flavor solution moves upward in the supply pipe is decreased. Under such a situation, even if the flavor solution is heated by the heater for a constant heating duration, the supply amount of the flavor solution supplied from the supply pipe into the inhalation passage, that is, the production of the flavored aerosol is reduced. As a result, the production of the flavored aerosol becomes unstable.

Furthermore, the liquid tank needs to be open into air through an air vent, so that there is the possibility that the flavor solution in the liquid tank leaks through the air vent.

The liquid tank of Patent Document 2 includes a flexible bag filled with a flavor solution as a tank body, and the flexible bag is also connected to a supply position of an inhalation passage via a supply pipe. The flavor solution in the flexible bag is supplied via the supply pipe to the inhalation passage through inhalation pressure in the inhalation passage. Since the flexible bag can change in shape, the pressure in the flexible bag is always maintained equal to atmosphere pressure and stays constant. The amount of the flavor solution supplied from the flexible bag is determined by the inhalation pressure, so that the flexible bag enables a stable supply of the flavor solution and prevents the leakage of the flavor solution without fail.

The stable supply of the flavor solution is achieved only if the flexible bag contains a sufficient amount of the flavor solution. If the remaining amount of the flavor solution in the flexible bag becomes small, more force is required for shrinkage of the flexible bag itself, and the supply of the flavor solution is not maintained to be stable. Moreover, neither the liquid tank of Patent Document 1 nor that of Patent Document 2 is capable of supplying all the flavor solution in the liquid tank. In other words, the liquid tank is discarded with the flavor solution remaining inside or has to be refilled with the flavor solution.

It is an object of the invention to provide a liquid tank for an aerosol inhalator which prevents a flavor solution from leaking and remaining and also enables a stable supply of the flavor solution.

Means for Solving the Problem

The above object is accomplished by a liquid tank of the invention. The liquid tank comprises a reservoir channel containing flavor solution and including one end provided with an air vent which opens into air and the other end; a supply pipe connecting the other end of the reservoir channel and an inhalation passage to each other, the supply pipe having cross-sectional area smaller than that of the reservoir channel, including a supply port which opens into the inhalation passage, and guiding the flavor solution from the reservoir channel to the supply port through either one of inhalation pressure and capillary action in the inhalation passage; and an outflow valve located between the other end of the reservoir channel and the supply pipe, for allowing only a flow of the flavor solution running from the reservoir channel towards the supply pipe.

In the above-mentioned liquid tank, in response to the generation of inhalation pressure in the inhalation passage, the flavor solution in the reservoir channel is sucked from the supply port of the supply pipe into the inhalation passage according to differential pressure between the inhalation pressure at the supply port and atmosphere pressure at the air vent. At the same time that the flavor solution is sucked out, the flavor solution in the reservoir channel is resupplied into the supply pipe via the outflow valve. Accordingly, the supply port of the supply pipe is constantly being supplied with the flavor solution.

Every time the inhalation pressure is generated in the inhalation passage, the supply of the flavor solution into the inhalation passage and the resupply of the flavor solution from the reservoir channel into the supply pipe take place, and the flavor solution in the reservoir channel moves towards the supply pipe. The flavor solution in the reservoir channel is therefore all supplied into the inhalation passage.

Unless the differential pressure is generated, the flavor solution in the reservoir channel receives the atmosphere pressure through the supply port and the air vent. Nevertheless, as long as the flavor solution and the reservoir channel have a certain level of viscosity and channel resistance, respectively, the flavor solution is prevented from moving within the reservoir channel, regardless of the posture of the liquid tank. The flavor solution is thus prevented without fail from leaking through the supply port of the supply pipe or the air vent of the reservoir channel.

More specifically, the flavor solution has viscosity equal to or lower than 1499 mPa·s at room temperature based upon the Japanese Industrial Standards, and the reservoir channel has cross-sectional area equal to or smaller than 38 mm$^2$. Preferably, the flavor solution has viscosity equal to or lower than 61 mPa·s at room temperature based upon the Japanese Industrial Standards, and the reservoir channel has cross-sectional area equal to or smaller than 28 mm$^2$. More preferably, the supply pipe has cross-section area equal to or smaller than 0.1 mm$^2$.

The liquid tank may further include an inflow valve. The inflow valve is located in the reservoir channel close to the air vent and allows only a flow of the air running from the air vent into the reservoir channel. The inflow valve reliably prevents the flavor solution from leaking through the air vent.

The liquid tank may include plug liquid instead of the inflow valve. The plug liquid is located in and blocks the reservoir channel at a position between the air vent and the flavor liquid contained in the reservoir channel. In this case, the plug liquid does not possess an affinity for the flavor solution and is located adjacent to the flavor solution. Alternatively, the liquid tank is further provided in the reservoir channel with an air layer for separating the plug liquid and the flavor solution from each other.

The plug liquid moves in conjunction with the movement of the flavor solution within the reservoir channel and transmits the atmosphere pressure to the flavor solution. At the same time, the plug liquid prevents the dust, which enters the reservoir channel through the air vent, from being mixed into the flavor solution.

Specifically, a part of the reservoir channel may be a coil tube or a passage extending in a manner reciprocating along a reference axis.

Technical Advantage of the Invention

The liquid tank of the invention is capable of not only stably supplying the flavor solution to the inhalation passage but also reliably preventing the leakage of the flavor solution from the supply port of the supply pipe and the air vent of the reservoir channel and the undesired remaining of the flavor solution in the reservoir channel.

BEST MODE OF CARRYING OUT THE INVENTION

Figure 1:
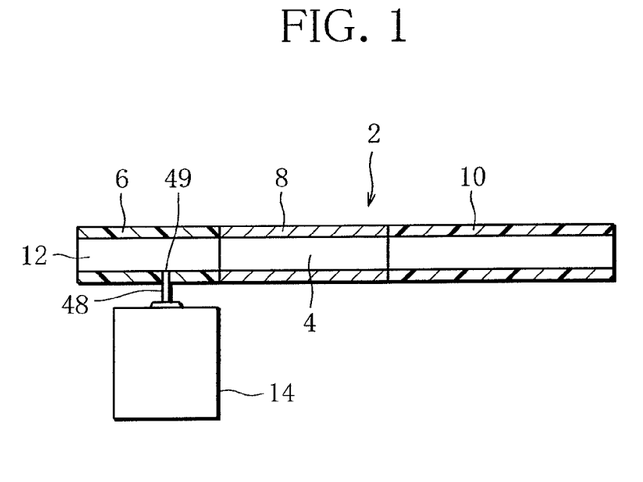
FIG. 1 is a schematic illustration for explaining a basic principle of an aerosol inhalator.

An aerosol inhalator shown in FIG. 1 comprises a pipe member 2. The interior of the pipe member 2 is formed as an inhalation passage 4. The pipe member 2 includes an air-entering section 6, a heating section 8, and a mouthpiece section 10 arranged in the order named from one end thereof. The air-entering section 6, namely, the inhalation passage 4, has an air intake opening 12 which opens into air at the one end of the pipe member 2.

Connected to the air-entering section 6 is a liquid tank 14. The liquid tank 14 contains a flavor solution. The flavor solution is a material for making flavored aerosol.

When the user inhales air through the mouthpiece section 10, inhalation pressure is generated in the inhalation passage 4. The inhalation pressure creates air that flows from the air intake opening 12 towards the mouthpiece section 10, and also causes the flavor solution to be sucked out from the liquid tank 14 into the inhalation passage 4. After being sucked out, the flavor solution moves to the heating section 8 along with the air flow. The flavor solution is then evaporated by the heating section 8 and condensed in the air flow. In this manner, flavored aerosol is produced. This way, the user can inhale the flavored aerosol with air and taste the flavor of the flavored aerosol.

Figure 2:
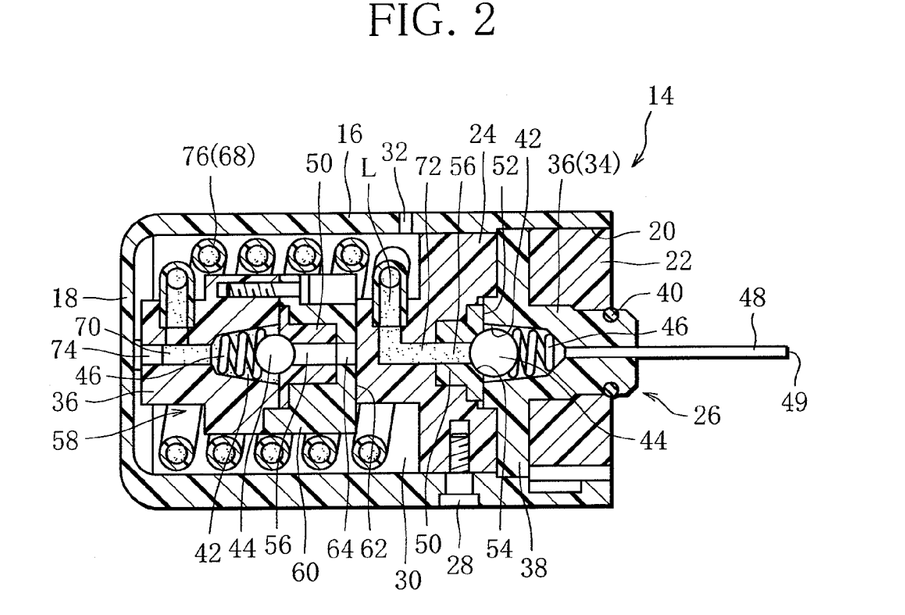
FIG. 2 is a cross-sectional view showing a first embodiment of a liquid tank of FIG. 1.

FIG. 2 shows the liquid tank 14 of a first embodiment. The liquid tank 14 has an axis that extends along a longitudinal axis of the aerosol inhalator when installed in the aerosol inhalator.

The liquid tank 14 includes a housing 16. The housing 16 has a shape of a hollow cylinder extending along the axis of the liquid tank 14 and has a closed end 18 and an open end 20. The open end 20 is closed with an end wall 22. The end wall 22 holds an outflow valve 26 in cooperation with a partition wall 24 located inside the housing 16 so that the outflow valve 26 is sandwiched between the end wall 22 and the partition wall 24. The partition wall 24 divides the inside of the housing 16 and is fixed onto a circumferential wall of the housing 16 with a plurality of screws 28. FIG. 2 shows only one of the screws 28. Inside the housing 16, an inner chamber 30 is defined between the closed end 18 and the partition wall 24. The inner chamber 30 opens into air through a plurality of air holes 32.

The outflow valve 26 includes a valve casing 34. The valve casing 34 has a cylindrical body 36 and a flange 38 extending from the body 36 in a radially outward direction. The flange 38 is sandwiched between the end wall 22 and the partition wall 24. The body 36 has an outer end protruding from the end wall 22. A gap between the outer end and the end wall 22 is sealed with an O-ring 40. A valve chamber 42 is defined in the body 36. The valve chamber 42 is formed into a tapered hole. This tapered hole opens in an inner end face of the body 36 and is tapered from the inner end face towards the outer end of the body 36.

A ball 44 serving as valve elements and a valve spring 46 are arranged in the valve chamber 42 in the order named from the inner end face of the valve casing 34. The valve spring 46 is made of a coil spring and urges the ball 44 in a direction of pushing the ball 44 out of the valve chamber 42. A supply pipe 48 is arranged in the body 36. The supply pipe 48 extends from the valve chamber 42 and is protruding from the outer end of the body 36.

The outflow valve 26 further includes a valve seat member 50. The valve seat member 50 has a shape of a stepped cylinder and is held inside the partition wall 24. The valve seat member 50 has a large-diameter end 52 and a small-diameter end. The large-diameter end 52 is in close contact with the inner end face of the body 36, to thereby close the valve chamber 42. A hemispherical valve seat 54 is formed in an end face of the large-diameter end 52. The valve seat 54 allows the ball 44 to seat thereagainst. A through-hole 56 is formed in the valve seat member 50. The through-hole 56 opens in the center of the valve seat 54 and the end face of the small-diameter end of the valve seat member 50. The valve chamber 42 and the through-hole 56 form a valve passage for the outflow valve 26.

The outflow valve 26 is a check valve which allows only a flow running from the through-hole 56 towards the valve chamber 24.

An inflow valve 58 is installed in the inner chamber 30. The inflow valve 58 is placed between a valve seat holder 60 and the closed end 18 of the housing 16. The valve seat holder 60 is formed into a cylinder and has an end face 62 in close contact with the partition wall 24. An air intake groove 64 is formed in the end face 62. The air intake groove 64 extends in a radial direction of the valve seat holder 60 and opens in an outer periphery of the valve seat holder 60 as an air vent. The air intake groove 64 leads to air through the inner chamber 30 and the air holes 32.

The inflow valve 58 has the same structure as the outflow valve 26. In order to avoid the repetition of explanation, members of the inflow valve 58, which have the same functions as those of the outflow valve 26, are provided with the same reference marks.

As to the inflow valve 58, therefore, only differences from the outflow valve 26 will be explained below.

The inflow valve 58 is disposed to face opposite to the outflow valve 26. The through-hole 56 of the inflow valve 58 is connected to the air intake groove 64. The valve holder 60 and the body 36 of the inflow valve 58 are jointed together via a plurality of screws 66.

The inflow valve 58 and the outflow valve 26 are connected to each other via a reservoir channel 68. The reservoir channel 68 will be described below in detail.

The reservoir channel 68 includes internal passages 70 and 72 formed in the inflow valve 58 and the body 36 of the outflow valve 26. The internal passages 70 and 72 each have one end which opens into the valve chamber 42 of the corresponding valve and the other end which opens in the outer periphery of the body 36. The internal passage 70 has an inlet which opens in the end face of the body 36. The inlet is closed with a plug 74.

The reservoir channel 68 further includes a coil tube 76 which connects the other end of the internal passage 70 to that of the internal passage 72. The coil tube 76 is so disposed as to surround the inflow valve 58 and extends inside the inner chamber 30 in the axis direction of the liquid tank 14.

When the liquid tank 14 is in an initial state, the inside of a liquid supply line formed of the valve chamber 42 of the inflow valve 58, the reservoir channel 68, the valve chamber 42 of the outflow valve 26, and the supply pipe 48 is filled with a flavor solution L, based on the inhalation pressure or capillary action in the inhalation passage 4. The flavor solution L is guided to a tip end of the supply pipe 48. The supply pipe 48 has a cross-sectional area substantially smaller than an average cross-sectional area of the reservoir channel 68. The flavor solution L can be poured into the liquid channel through the inlet.

When the liquid tank 14 is installed in the aerosol inhalator, the tip end of the supply pipe 48 is positioned inside the inhalation passage 4 of the aerosol inhalator as a supply port 49. When the user inhales air in the inhalation passage 4 from the mouthpiece section 10 of the aerosol inhalator, inhalation pressure is generated in the inhalation passage 4. The inhalation pressure opens the outflow valve 26 and the inflow valve 58, and causes the flavor solution L to be sucked out from the supply port 49 of the supply pipe 48 into the inhalation passage 4.

If the flavor solution L in the reservoir channel 68 is considered as a continuum, inhalation amount of the flavor solution L, namely, supply amount of the flavor solution L to the inhalation passage 4, is determined by differential pressure between the inhalation pressure acting upon a distal end face (supply port 49 of the supply pipe 48) of the continuum and the atmospheric pressure acting upon a rear end of the continuum and an inhalation duration. As the sucking out of the flavor solution L from the supply pipe 48, the continuum of the flavor solution L proceeds in the reservoir channel 68 towards the supply port 49 of the supply pipe 48. The supply port 49 of the supply pipe 48 is thus constantly filled with the flavor solution L.

For that reason, each time the user inhales, the flavor solution L is supplied into the inhalation passage 4, and the continuum of the flavor solution L proceeds. The liquid tank 14 therefore stably supplies the flavor solution L into the inhalation passage 4. The flavor solution L in the reservoir channel 68 is all supplied into the inhalation passage 4, so that the flavor solution L does not undesirably remain in the reservoir channel 68.

When the inhalation pressure is not generated in the inhalation passage 4, the outflow valve 26 and the inflow valve 58 are each in a closed position, so that there is no possibility that the flavor solution L leaks from the supply port 49 of the supply pipe 48 or the inflow valve 58.

Figure 3:
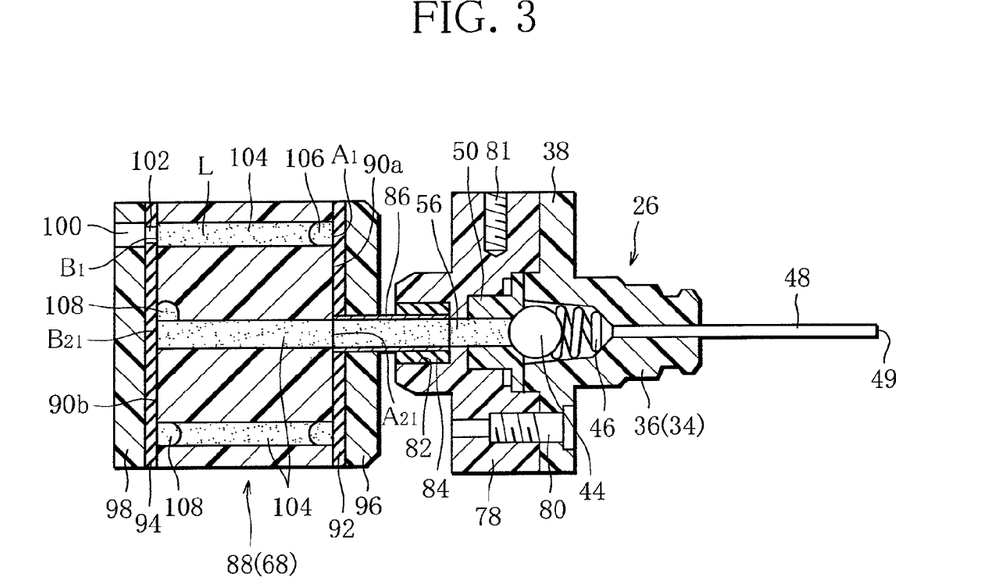
FIG. 3 is a cross-sectional view showing a second embodiment of the liquid tank.

FIG. 3 shows the liquid tank 14 of a second embodiment.

In the description of the second embodiment, members and portions having the same functions as those of the first embodiment will be provided with the same reference marks.

The second embodiment will be described below, focusing on differences from the first embodiment.

The outflow valve 26 of the second embodiment is held by a valve seat holder 78. The valve seat holder 78 performs the same function as the partition wall 24 of the first embodiment. The valve seat holder 78 and the flange 38 of the valve casing 34 are jointed together with a plurality of screws 80. The valve seat holder 78 has a screw hole 81 in an outer periphery thereof. If the liquid tank 14 of the second embodiment has the housing 16, the screw hole 81 is used for screwing a screw therein for connecting the housing 16 with the valve seat holder 78.

The valve seat holder 78 has a stepped hole 82 in a face opposite to the valve casing 34. The stepped hole 82 leads to the through-hole 56 of the valve seat member 50. One end of a connecting pipe 86 forming a downstream region of the reservoir channel 68 is inserted in the stepped hole 82 via a seal ring 84. The other end of the connecting pipe 86 is connected to a reservoir assembly 88 for forming an upstream region of the reservoir channel 68 in the inside thereof.

More specifically, the reservoir assembly 88 includes a cylindrical block 90. The block 90 has one end face 90a and the other end face 90b. Circular end walls 96 and 98 are attached to the end faces 90a and 90b via seal plates 92 and 94, respectively. The connecting pipe 86 extends through the center of the end wall 96 and the seal plate 92. The other end of the connecting pipe 86 is in close contact with the end face 90a of the block 90.

An air vent 100 and a throttle hole 102 of the reservoir channel 68 are formed in outer periphery portions of the end wall 98 and the seal plate 94, respectively. The air vent 100 and the throttle hole 102 lead to each other. The throttle hole 102 has an inner diameter smaller than the inner diameter of the air vent 100.

In the block 90, there is formed a connecting passage which connects the throttle hole 102 to the other end of the connecting pipe 86. The connecting passage forms the rest of the reservoir channel 68 and extends in a manner reciprocating along the axis of the block 90. The connecting passage includes a large number of through-holes 104 formed in the block 90. The through-holes 104 extend through the block 90 along the axis direction of the block 90 and each have openings A and B that open in the end faces 90a and 90b, respectively.

Figure 4:
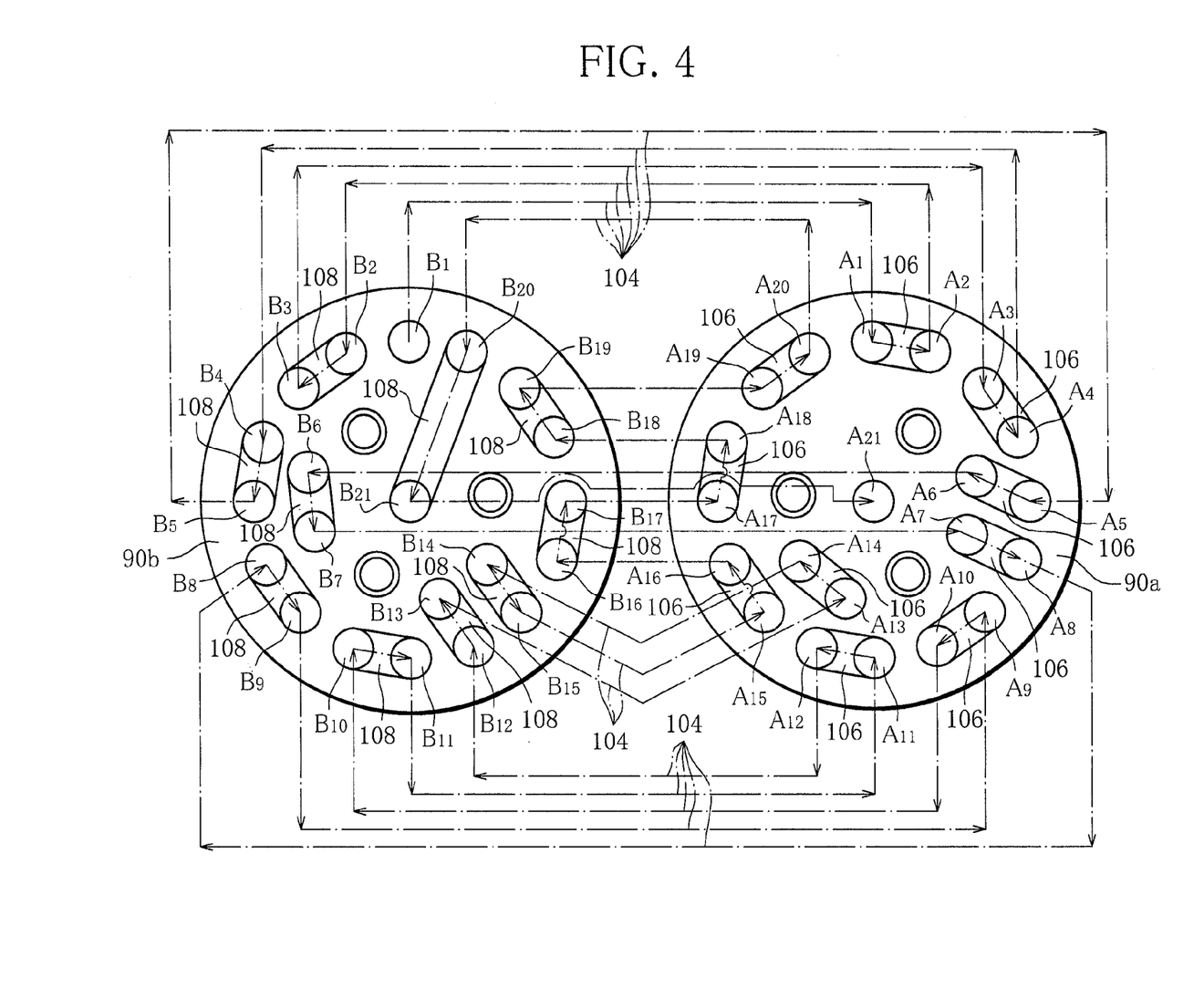
FIG. 4 shows both end faces of a reservoir block of FIG. 3.

FIG. 4 shows distribution of the openings A and B in the end faces 90a and 90b. Each of the through-holes 104 has the openings A and B with an identical numeral subscript. In FIG. 4, the through-holes 104 are shown by dashed lines.

A large number of grooves 106 are formed in the end face 90a. The grooves 106 connect an opening A1 to an opening A2, A3 to A4, A5 to A6, A7 to A8, A9 to A10, A11 to A12, A13 to A14, A15 to A16, A17 to A18, and A19 to A20, respectively.

Formed in the end face 90b are a large number of grooves 108. The grooves 108 connect an opening B2 to B3, B4 to B5, B6 to B7, B8 to B9, B10 to B11, B12 to B13, B14 to B15, B16 to B17, B18 to B19, and B20 to B21, respectively.

The through-hole 104 with the openings A1 and B1 is disposed in the outer periphery of the block 90. The opening B1 of the through-hole 104 is connected to the air vent 100 through the throttle hole 102. The through-hole 104 with the openings A21 and B21 is located in the axis of the block 90. The opening A21 of the through-hole 104 is connected to the other end of the connecting pipe 86.

As is apparent from arrows added to the dashed lines in FIG. 4, the through-holes 104 and the grooves 106 and 108 form a single connecting passage connecting the throttle hole 102 to the connecting pipe 86.

When the liquid tank 14 is in the initial state, the inside of the liquid supply line extending from the connecting passage through the connecting pipe 86 and the outflow valve 26 to the supply port 49 of the supply pipe 48 is filled with the flavor solution L. In the second embodiment, the flavor solution L is poured from the air vent 100.

Even if the reservoir channel 68 opens directly into air at the air vent 100, the liquid tank 14 of the second embodiment performs the same function as the liquid tank 14 of the first embodiment, and the flavor solution L does not leak from the air vent 100, as long as the viscosity of the flavor solution L and the cross-sectional areas of the reservoir channel 68 and the supply pipe 40 are properly determined.

Figure 5:
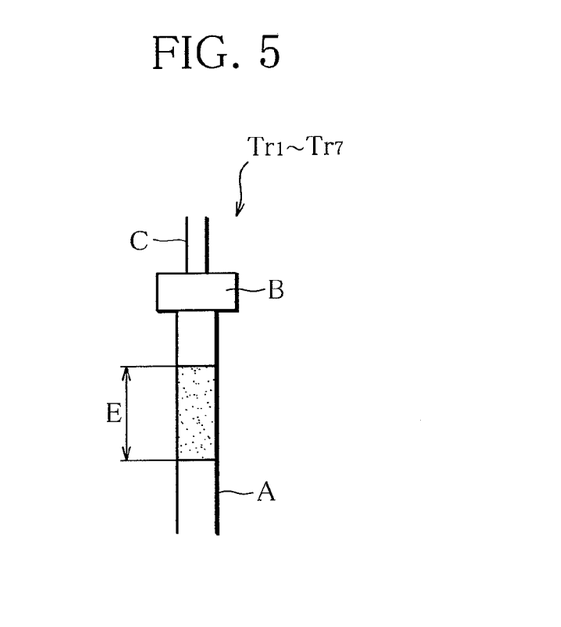
FIG. 5 is a schematic view of testers Tr.

For the purpose of verifying this, testers Tr1 to Tr7 as shown in FIG. 5 were prepared. The testers Tr each have a Teflon tube A, check valve B and narrow tube C corresponding to the reservoir channel 68, the outflow valve 26 and the supply pipe 48, respectively. Only the inner diameter of the tube A is different in the testers Tr.

The tube A of each of the testers Tr contains only a predetermined amount of one of liquids D1 to D4 through suction, respectively. The liquids D each have a length E of 30 mm. The liquids D1 to D4 represent water (W), aqueous solution of propylene glycol (PG) (W:PG=1:1 on a weight basis), propylene glycol (PG), and glycerin (G), respectively.

The testers Tr were let stand for a predetermined time period (30 seconds, for example) under conditions 1 to 3 below. In this manner, a test was conducted, which examines whether the leakage of the liquids D from the tube A was observed.

Condition 1: During the test, the testers Tr were in a position vertically suspended with the narrow tube C positioned upside.

Condition 2: During the test, the testers Tr were in a horizontal position with the tube A horizontally positioned.

Condition 3: During the test, the testers Tr were in a vertical position without the check valve B.

The results of the above test are shown in TABLE 1 below.

TABLE 1

|  | ID (mm) | SA (mm$^2$) | Condition 1 | | | | Condition 2 | | | | Condition 3 | | | |
| --- | --- | --- | --- | --- | --- | --- | --- | --- | --- | --- | --- | --- | --- | --- |
|  |  |  | W | PGL | PG | G | W | PGL | PG | G | W | PGL | PG | G |
| Tr1 | 0.8 | 0.5 | ○ | ○ | ○ | ○ | ○ | ○ | ○ | ○ | X | X | X | ○ |
| Tr2 | 1.59 | 2.0 | ○ | ○ | ○ | ○ | ○ | ○ | ○ | ○ | X | X | X | X |
| Tr3 | 4 | 12.6 | ○ | ○ | ○ | ○ | ○ | ○ | ○ | ○ | X | X | X | X |
| Tr4 | 6 | 28.3 | ○ | ○ | ○ | ○ | ○ | ○ | ○ | ○ | X | X | X | X |
| Tr5 | 7 | 38.5 | ○ | ○ | ○ | ○ | ○ | X | ○ | X | X | X | X | X |
| Tr6 | 8 | 50.3 | ○ | ○ | ○ | ○ | X | X | X | X | X | X | X | X |
| Tr7 | 9 | 95.0 | X | X | X | X | X | X | X | X | X | X | X | X |

In TABLE 1, ID and SA represent an inner diameter and cross-sectional area, respectively, of the tube A. In TABLE 1, ○ means that the liquid D did not move or leak within and from the tube A, and X means that the liquid D moved or leaked.

Comparing Conditions 1 and 2 with Condition 3, as is evident from TABLE 1, the existence of the check valve B, namely, the existence of the outflow valve 26 located between the reservoir channel 68 and the supply pipe 48, is effective in greatly reducing the risk of leakage of the flavor solution L from the air vent 100 even if the liquid tank 14 of FIG. 3 is inclined.

When the liquid D, namely, the flavor solution L, has a viscosity equal to or lower than 1499 mPa·s at a temperature of 20 degrees centigrade as seen in glycerin (G) or the like, the leakage of the flavor solution L is further effectively prevented on the condition that the tube A, or the reservoir channel 68, has cross-sectional area equal to or smaller than 38 mm$^2$ (the reservoir channel 68 has an inner diameter smaller than 7 mm). On the other hand, since the flavor solution L is aerosolized by being heated, glycerin requires much thermal energy to be aerosolized due to its high boiling point.

In this respect, when the flavor solution L is a solution of propylene glycol (PG) or the like, which has a lower boiling point than glycerin and has viscosity equal to or lower than 60.5 mPa·s at a temperature of 20 degrees centigrade, it is preferable that the reservoir channel 68 have cross-sectional area equal to or smaller than 28 mm² (the reservoir channel has an inner diameter smaller than 6 mm) to effectively prevent the leakage of the flavor solution L.

Figure 6:
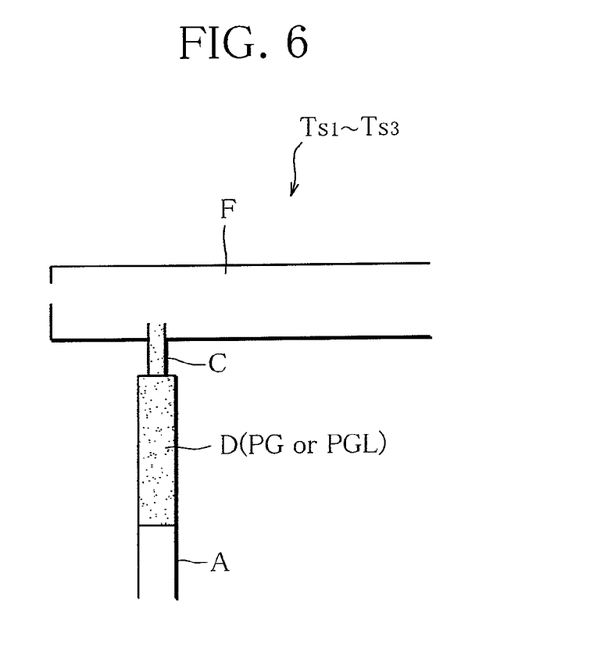
FIG. 6 is a schematic view of testers Ts.

In order to verify the delivery of the flavor solution L from the supply pipe 48, testers Ts1 to Ts3 shown in FIG. 6 were prepared.

The testers Ts correspond to the testers Tr in which the check valve B is removed, and the narrow tube C is connected to a inhalation tube F. Although the tubes A of the testers Ts1 to Ts3 are the same, the narrow tubes C are different from each other in inner diameter. The inhalation tube F corresponds to the inhalation passage 4 and is provided in a tip end thereof with an orifice corresponding to the air intake opening 12.

Under the condition that the tubes A and the narrow tubes C of the testers Ts1 to Ts3 were filled with a predetermined amount of the liquid D (PG or PGL), and that the testers Ts were placed in a horizontal position, a inhalation test was carried out, in which the air in the inhalation tube F was inhaled under predetermined inhalation conditions. Thereafter, the supply amount of the liquid D supplied from the narrow tube C into the inhalation tube F by the inhalation test was measured. The actual inhalation test repeated the inhalation of air in the inhalation tube F ten times, and obtained total supply amount of the liquid D supplied from the narrow tube C. Based upon the total supply amount, the supply amount of the liquid D supplied through one inhalation action was calculated. During the inhalation action, the pressure in the inhalation tube F was maintained at 100 mmAq under the inhalation condition of 35 ml/2 sec.

TABLE 2 below shows the results of the inhalation test described above.

TABLE 2

|  | | C | | | | Inhalation Condition | |
|---|---|---|---|---|---|---|---|
|  | ID of A (mm) | ID (mm) | SA (mm²) | D | | 35 ml/ 2 sec | 55 m/ 2 sec |
| Ts1 | 1.59 | 0.14 | 0.015 | PGL | Supply Amount Q | 0.60 mg/puff | 1.29 mg/puff |
|  |  |  |  | PG |  | No Delivery | 0.04 mg/puff |
| Ts2 | 1.59 | 0.3 | 0.071 | PGL |  | 5.55 mg/puff | 13.09 mg/puff |
|  |  |  |  | PG |  | 1.11 mg/puff | 1.68 mg/puff |
| Ts3 | 1.59 | 0.5 | 0.196 | PG |  | 5.36 mg/puff | 11.92 mg/puff |

In TABLE 2, ID and SA represent the inner diameter and the cross-sectional area, respectively.

During the inhalation action, the liquid D in the tube A was maintained in a form of a continuous liquid column.

It is considered that the amount of the aerosol produced at inhalation using the testers Ts, namely aerosol inhalator, corresponds to the amount of tar generated from a cigarette at cigarette smoking. In general, the number of inhalation per cigarette, namely, the number of puffs, is approximately eight. Cigarettes, in which tar-delivery amount is high, deliver 20 mg of tar per cigarette. In this case, the tar-delivery amount per puff is 2.5 mg.

Assuming the liquid D is all aerosolized, as is clear from TABLE 2, when the liquid D is PG, it is preferable that the narrow C, namely, the supply pipe 48, have cross-sectional area equal to or smaller than 0.1 mm².

Figure 7:
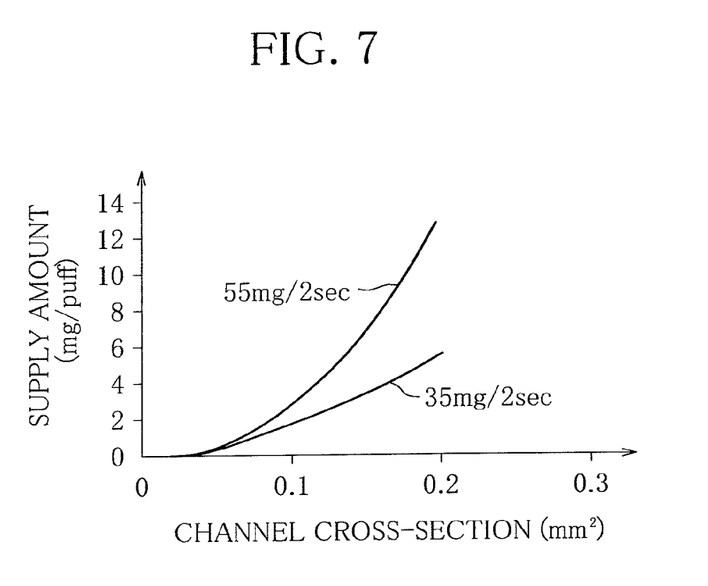
FIG. 7 is a graph showing relationship between a channel cross-section of a narrow tube and a liquid supply amount in the testers Ts.

FIG. 7 shows relationship between the cross-sectional area of the narrow tube C and PG supply amount under the above-mentioned inhalation conditions. As is obvious from FIG. 6, when the narrow tube C has the cross-sectional area of 0.1 mm², PG supply amounts are 2.98 mg/puff and 2.58 mg/puff under the inhalation conditions of 55 ml/2 sec and 35 ml/2 sec, respectively.

Figure 8:
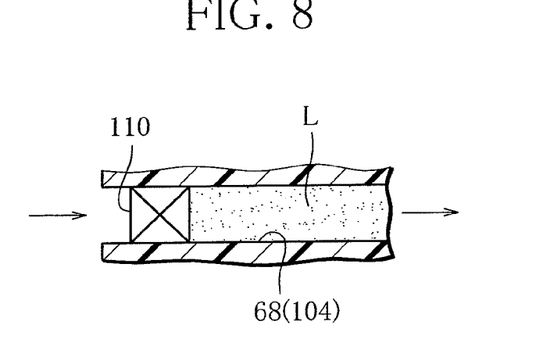
FIG. 8 is a cross-sectional view showing a part of a reservoir channel including plug liquid.

In the second embodiment, there is the possibility that dust enters the connecting passage through the air vent 100, and thus that the flavor solution L gets contaminated with the dust or the like. To avoid this, the liquid tank 14 of the second embodiment may further include plug liquid 110 which is poured into the reservoir channel 68 (through-holes 104) and blocks the reservoir channel 68, as shown in FIG. 8. The plug liquid 110 does not possess an affinity for the flavor solution L and is positioned adjacent to the rear end of the continuum of the flavor solution L. As a result, the plug liquid 110 proceeds with the continuum of the flavor solution L and reliably prevents the contamination of the flavor solution L, attributable to dust or the like.

Figure 9:
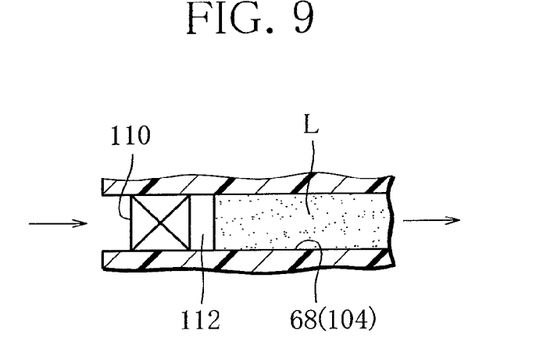
FIG. 9 is a cross-sectional view showing a part of a reservoir channel including plug liquid and an air layer.

As shown in FIG. 9, the liquid tank 14 of the second embodiment may further include an air layer 112 between the plug liquid 110 and the rear end of the continuum of the flavor solution L. In this case, the plug liquid 110 is not required to possess an affinity for the flavor solution L.

The invention is not limited to the liquid tank of the first and second embodiments. The specific configuration of the outflow valve 26, the inflow valve 58 and the reservoir region may be modified in various ways. The supply pipe 48 of the liquid tank 14 may be a capillary which guides the flavor solution L to the tip end thereof through capillary action without using the inhalation pressure in the inhalation passage.

REFERENCE MARKS 26 outflow valve
48 supply pipe
49 supply port
58 inflow valve
64 air intake groove
68 reservoir channel
76 coil tube
88 reservoir assembly
100 air vent
110 plug liquid
112 air layer
L flavor solution

The invention claimed is:

1. A liquid tank for an aerosol inhalator which transforms flavor solution into flavored aerosol in an air inhalation passage and allows inhalation of the flavored aerosol along with air, the liquid comprising:
   a reservoir channel containing the flavor solution and including one end provided with an air vent which opens into air and the other end;
   a supply pipe connecting the other end of said reservoir channel and the inhalation passage to each other, said supply pipe having cross-sectional area smaller than that of said reservoir channel, including a supply port which opens into the inhalation passage, and guiding the flavor solution from said reservoir channel to the supply port through either one of inhalation pressure and capillary action in the inhalation passage;
   an outflow valve located between the other end of said reservoir channel and said supply pipe, for allowing only a flow of the flavor solution running from said reservoir channel towards said supply pipe; and plug liquid situated in and blocks said reservoir channel at a position between the air vent and the flavor liquid contained in said reservoir channel.

2. The liquid tank according to claim 1, wherein the liquid tank further comprises an inflow valve located in said reservoir channel close to the air vent, for allowing only the flow of the air running from the air vent into said reservoir channel.

3. The liquid tank according to claim 1, wherein said plug liquid does not possess an affinity for the flavor solution and is located adjacent to the flavor solution.

4. The liquid tank according to claim 1, wherein the liquid tank is further provided in said reservoir channel with an air layer for separating said plug liquid and the flavor solution from each other.

5. The liquid tank according to claim 1, wherein the flavor solution has viscosity equal to or lower than 1499 mPa·s at room temperature based upon the Japanese Industrial Standards, and said reservoir channel has a cross-sectional area equal to or smaller than 38 mm².

6. The liquid tank according to claim 1, wherein the flavor solution has viscosity equal to or lower than 61 mPa·s at room temperature based upon the Japanese Industrial Standards, and said reservoir channel has a cross-sectional area equal to or smaller than 28 mm².

7. The liquid tank according to claim 6, wherein said supply pipe has a cross-sectional area equal to or smaller than 0.1 mm².

8. The liquid tank according to claim 1, wherein a part of said reservoir channel is a coil tube.

9. The liquid tank according to claim 1, wherein a part of said reservoir channel is a passage extending in a manner reciprocating along a reference axis.

* * * * *